(12) United States Patent
Cadieux, Jr. et al.

(10) Patent No.: US 10,209,201 B2
(45) Date of Patent: *Feb. 19, 2019

(54) OIL DETECTION PROCESS AND APPARATUS

(71) Applicant: Altria Client Services LLC, Richmond, VA (US)

(72) Inventors: Edmond J. Cadieux, Jr., Mechanicsville, VA (US); William James Faenza, Andreas, PA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,205

(22) Filed: Oct. 27, 2017

(65) Prior Publication Data

US 2018/0045655 A1    Feb. 15, 2018

Related U.S. Application Data

(60) Division of application No. 15/653,377, filed on Jul. 18, 2017, which is a continuation of application No.
(Continued)

(51) Int. Cl.
    *C07D 209/00*      (2006.01)
    *G01T 1/167*      (2006.01)
    (Continued)

(52) U.S. Cl.
CPC ........... *G01N 21/94* (2013.01); *A24C 5/3412* (2013.01); *B07C 5/3427* (2013.01); *C09K 11/06* (2013.01); *C09K 11/7769* (2013.01); *C10L 1/003* (2013.01); *C10M 171/007* (2013.01); *G01N 21/643* (2013.01); *G01N 21/88* (2013.01); *G01N 33/2882* (2013.01); *B07C 2501/009* (2013.01);
(Continued)

(58) Field of Classification Search
CPC .................... C10M 2215/064; G01N 33/1833
USPC .......................................... 508/296; 250/301
See application file for complete search history.

(56) References Cited

U.S. PATENT DOCUMENTS 3,085,581 A    4/1963   Rosenberg et al.
3,417,241 A    12/1968   Davis
(Continued)

FOREIGN PATENT DOCUMENTS

CA      2837315 A1    11/2012
DE      20320957 U1    7/2005
(Continued)

OTHER PUBLICATIONS

International Search Report of International Application No. PCT/US2014/026556 dated Aug. 5, 2014.
(Continued)

*Primary Examiner* — Vishal V Vasisth
(74) *Attorney, Agent, or Firm* — Harness, Dickey & Pierce, P.L.C.

(57) ABSTRACT

An inspection station for detecting oil or lubricant contamination in a manufactured product, the inspection station having (a) a conveyor for advancing manufactured product, and (b) an infrared detection apparatus, including (i) a high intensity infrared light source for directing at the manufactured product, and (ii) a high speed NIR spectrometer sensor tuned to detect an emitted signal from a taggant disposed in the oil or lubricant.

21 Claims, 8 Drawing Sheets

Related U.S. Application Data

14/994,972, filed on Jan. 13, 2016, now Pat. No. 9,733,197, which is a division of application No. 13/482,771, filed on May 29, 2012, now Pat. No. 9,244,017, which is a continuation-in-part of application No. 13/338,971, filed on Dec. 28, 2011, now Pat. No. 9,080,987.

(60) Provisional application No. 61/490,403, filed on May 26, 2011.

(51) Int. Cl.

| | |
|---|---|
| *G01T 1/169* | (2006.01) |
| *G01N 21/94* | (2006.01) |
| *B07C 5/342* | (2006.01) |
| *C09K 11/06* | (2006.01) |
| *C09K 11/77* | (2006.01) |
| *C10L 1/00* | (2006.01) |
| *C10M 171/00* | (2006.01) |
| *G01N 21/64* | (2006.01) |
| *G01N 21/88* | (2006.01) |
| *G01N 33/28* | (2006.01) |
| *A24C 5/34* | (2006.01) |
| *G01N 21/359* | (2014.01) |
| *G01N 33/02* | (2006.01) |
| *G01N 33/18* | (2006.01) |
| *G01N 21/84* | (2006.01) |

(52) U.S. Cl.
CPC .......... *B07C 2501/0081* (2013.01); *C09K 2211/1029* (2013.01); *C10M 2219/044* (2013.01); *C10N 2240/56* (2013.01); *G01N 21/359* (2013.01); *G01N 33/02* (2013.01); *G01N 33/18* (2013.01); *G01N 2021/6439* (2013.01); *G01N 2021/845* (2013.01); *G01N 2021/8416* (2013.01); *G01N 2021/8466* (2013.01); *G01N 2201/061* (2013.01)

(56) References Cited

U.S. PATENT DOCUMENTS

| | | |
|---|---|---|
| 3,806,727 A | 4/1974 | Leonard et al. |
| 3,812,349 A | 5/1974 | Gugliotta et al. |
| 3,880,289 A | 4/1975 | Gray |
| 3,985,581 A | 10/1976 | Stachurski et al. |
| 3,985,582 A | 10/1976 | Bibring et al. |
| RE29,298 E | 7/1977 | Banks |
| 4,057,721 A | 11/1977 | deVial et al. |
| 4,175,996 A | 11/1979 | Battard et al. |
| 4,445,520 A | 5/1984 | Knight et al. |
| 4,480,702 A | 11/1984 | Kelly, Jr. |
| 4,657,144 A | 4/1987 | Martin et al. |
| 4,845,374 A | 7/1989 | White et al. |
| 4,858,465 A | 8/1989 | Molina |
| 4,971,077 A | 11/1990 | Dominguez et al. |
| 5,048,543 A | 9/1991 | Smith |
| 5,092,349 A | 3/1992 | Smith et al. |
| 5,134,291 A | 7/1992 | Ruhl, Jr. et al. |
| 5,265,732 A | 11/1993 | Long |
| 5,440,919 A | 8/1995 | Cooper |
| 5,462,176 A | 10/1995 | Hereford et al. |
| 5,476,108 A | 12/1995 | Dominguez et al. |
| 5,525,516 A | 6/1996 | Krutak et al. |
| 5,554,480 A | 9/1996 | Patel et al. |
| 5,665,538 A | 9/1997 | Slater et al. |
| 5,710,046 A | 1/1998 | Rutledge et al. |
| 5,715,843 A | 2/1998 | Hapke et al. |
| 5,764,874 A | 6/1998 | White |
| 5,804,447 A | 9/1998 | Albert et al. |
| 5,807,605 A | 9/1998 | Tingey et al. |
| 5,846,830 A | 12/1998 | Demello et al. |
| 5,887,073 A | 3/1999 | Fazzari et al. |
| 5,974,860 A | 11/1999 | Kuroda et al. |
| 5,990,197 A | 11/1999 | Escano et al. |
| 5,998,211 A | 12/1999 | Albert et al. |
| 6,025,200 A | 2/2000 | Kaish et al. |
| 6,058,940 A | 5/2000 | Lane |
| 6,060,677 A | 5/2000 | Ulrichsen et al. |
| 6,064,032 A | 5/2000 | Voss et al. |
| 6,135,386 A | 10/2000 | Garthaffner |
| 6,149,719 A | 11/2000 | Houle |
| 6,166,366 A | 12/2000 | Lewis et al. |
| 6,312,958 B1 | 11/2001 | Meyer et al. |
| 6,380,547 B1 | 4/2002 | Gonzalez et al. |
| 6,384,359 B1 | 5/2002 | Belcastro et al. |
| 6,444,143 B2 | 9/2002 | Bawendi et al. |
| 6,477,227 B1 | 11/2002 | Kaiser et al. |
| 6,511,756 B1 | 1/2003 | Obuchi et al. |
| 6,529,273 B1 | 3/2003 | Norris et al. |
| 6,633,043 B2 | 10/2003 | Hegazi et al. |
| 6,734,383 B1 | 5/2004 | Calcoen et al. |
| 6,771,365 B1 | 8/2004 | Pirani et al. |
| 6,795,179 B2 | 9/2004 | Kumar |
| 6,809,819 B1 | 10/2004 | Vinjamoori et al. |
| 6,830,310 B2 | 12/2004 | Iu et al. |
| 6,905,538 B2 | 6/2005 | Auslander |
| 6,914,678 B1 | 7/2005 | Ulrichsen et al. |
| 6,926,764 B2 | 8/2005 | Bleikolm et al. |
| 7,124,944 B2 | 10/2006 | Selinfreund et al. |
| 7,142,296 B2 | 11/2006 | Cunningham et al. |
| 7,153,557 B2 | 12/2006 | Rancien |
| 7,157,611 B2 | 1/2007 | Banavali et al. |
| 7,227,148 B2 | 6/2007 | Sato et al. |
| 7,256,398 B2 | 8/2007 | Ross et al. |
| 7,319,039 B2 | 1/2008 | Sullivan |
| 7,378,675 B2 | 5/2008 | Ross et al. |
| 7,391,035 B2 | 6/2008 | Kong et al. |
| 7,441,704 B2 | 10/2008 | Ross |
| 7,488,945 B2 | 2/2009 | Li et al. |
| 7,538,324 B2 | 5/2009 | Deevi et al. |
| 7,705,144 B2 | 4/2010 | Holmes |
| 7,749,438 B2 | 7/2010 | Zeinali et al. |
| 7,767,457 B2 | 8/2010 | Mun et al. |
| 7,768,643 B1 | 8/2010 | Janssens et al. |
| 7,800,088 B2 | 9/2010 | Ross et al. |
| 7,812,953 B2 | 10/2010 | Tai et al. |
| 7,816,616 B2 | 10/2010 | Kenny et al. |
| 7,829,162 B2 | 11/2010 | Eskra et al. |
| 7,842,896 B1 | 11/2010 | Calcoen et al. |
| 7,919,325 B2 | 4/2011 | Eastwood et al. |
| 7,938,124 B2 | 5/2011 | Izumiya et al. |
| 7,985,590 B2 | 7/2011 | McNeil |
| 8,415,165 B2 | 4/2013 | Liang et al. |
| 8,641,933 B2 | 2/2014 | Purdy et al. |
| 8,692,148 B1 | 4/2014 | Sommer, Jr. et al. |
| 9,006,599 B2 | 4/2015 | Adams et al. |
| 9,073,091 B2 | 7/2015 | Cadieux et al. |
| 9,080,987 B2 | 7/2015 | Faenza |
| 9,097,668 B2 | 8/2015 | Cadieux et al. |
| 9,244,017 B2 | 1/2016 | Cadieux, Jr. et al. |
| 9,361,561 B2 | 6/2016 | Bown et al. |
| 9,546,966 B2 | 1/2017 | Cadieux, Jr. et al. |
| 9,733,197 B2 | 8/2017 | Cadieux, Jr. et al. |
| 9,791,407 B2 | 10/2017 | Urey et al. |
| 2001/0045378 A1 | 11/2001 | Charles et al. |
| 2002/0074269 A1 | 7/2002 | Hensley et al. |
| 2002/0094058 A1 | 7/2002 | Kaiser et al. |
| 2002/0097833 A1 | 7/2002 | Kaiser et al. |
| 2002/0122878 A1 | 9/2002 | Kerns et al. |
| 2002/0158212 A1 | 10/2002 | French et al. |
| 2003/0034282 A1 | 2/2003 | Safai |
| 2003/0036201 A1 | 2/2003 | Nelson et al. |
| 2003/0058990 A1 | 3/2003 | Kaiser et al. |
| 2003/0097833 A1 | 5/2003 | Ingram et al. |
| 2003/0129283 A1 | 7/2003 | Martinez Carballido |
| 2003/0141459 A1 | 7/2003 | Hegazi et al. |
| 2003/0183326 A1 | 10/2003 | O'Connor |
| 2003/0194052 A1 | 10/2003 | Price et al. |
| 2004/0134504 A1 | 7/2004 | Lane |
| 2005/0029469 A1 | 2/2005 | Schroder et al. |

(56) References Cited

U.S. PATENT DOCUMENTS

| | | |
|---|---|---|
| 2005/0031838 A1 | 2/2005 | Lagunowich et al. |
| 2005/0083720 A1 | 4/2005 | Fukui et al. |
| 2005/0092336 A1 | 5/2005 | Zielke et al. |
| 2005/0092408 A1 | 5/2005 | Lauf et al. |
| 2005/0099475 A1 | 5/2005 | Barreto |
| 2005/0236015 A1 | 10/2005 | Goel et al. |
| 2005/0241989 A1 | 11/2005 | Sant et al. |
| 2005/0276906 A1 | 12/2005 | Metzger |
| 2006/0016735 A1 | 1/2006 | Ito et al. |
| 2006/0081503 A1 | 4/2006 | Wegner |
| 2006/0118741 A1 | 6/2006 | Ross et al. |
| 2006/0131517 A1 | 6/2006 | Ross et al. |
| 2006/0131518 A1 | 6/2006 | Ross et al. |
| 2006/0186348 A1 | 8/2006 | Nguyen et al. |
| 2006/0246020 A1 | 11/2006 | Cole et al. |
| 2006/0262318 A1 | 11/2006 | Sullivan |
| 2006/0291872 A1 | 12/2006 | Mei et al. |
| 2007/0023715 A1 | 2/2007 | Ross et al. |
| 2007/0048761 A1 | 3/2007 | Reep et al. |
| 2007/0084269 A1 | 4/2007 | Quest et al. |
| 2007/0187617 A1 | 8/2007 | Kong et al. |
| 2007/0239367 A1 | 10/2007 | Odegard et al. |
| 2008/0030712 A1 | 2/2008 | Tokhtuev |
| 2008/0116272 A1 | 5/2008 | Giering et al. |
| 2008/0121815 A1 | 5/2008 | Agrawal et al. |
| 2009/0047531 A1 | 2/2009 | Bartley et al. |
| 2009/0097833 A1 | 4/2009 | Imada |
| 2009/0104711 A1 | 4/2009 | Sim |
| 2009/0185182 A1 | 7/2009 | Kim et al. |
| 2009/0280341 A1 | 11/2009 | Maruichi et al. |
| 2009/0321623 A1 | 12/2009 | Ross et al. |
| 2010/0080456 A1 | 4/2010 | Paul et al. |
| 2010/0163063 A1 | 7/2010 | Fernando et al. |
| 2010/0219377 A1 | 9/2010 | Ebert |
| 2010/0224795 A1 | 9/2010 | Cole et al. |
| 2010/0226861 A1 | 9/2010 | Cole et al. |
| 2010/0233447 A1 | 9/2010 | Campbell |
| 2010/0290040 A1 | 11/2010 | Berghmans |
| 2010/0320371 A1 | 12/2010 | Agrawal et al. |
| 2011/0141272 A1 | 6/2011 | Uto et al. |
| 2011/0151576 A1 | 6/2011 | Perfect et al. |
| 2011/0168915 A1 | 7/2011 | Yajima et al. |
| 2011/0216190 A1 | 9/2011 | Shimazu et al. |
| 2012/0104278 A1 | 5/2012 | Ebert |
| 2012/0267287 A1 | 10/2012 | Bailey |
| 2012/0302474 A1 | 11/2012 | Faenza |
| 2013/0082173 A1 | 4/2013 | Cadieux, Jr. et al. |
| 2013/0179090 A1 | 7/2013 | Conroy et al. |
| 2013/0188170 A1 | 7/2013 | Wilkins |
| 2013/0320216 A1 | 12/2013 | Aiko et al. |
| 2013/0320237 A1 | 12/2013 | Cadieux et al. |
| 2014/0262966 A1 | 9/2014 | Cadieux, Jr. |
| 2015/0008162 A1 | 1/2015 | Cadieux, Jr. |
| 2015/0048250 A1 | 2/2015 | Cadieux, Jr. et al. |
| 2015/0290684 A1 | 10/2015 | Cadieux, Jr. |
| 2015/0315511 A1 | 11/2015 | Faenza |
| 2015/0323459 A1 | 11/2015 | Cadieux, Jr. |
| 2016/0108293 A1 | 4/2016 | Cadieux, Jr. et al. |
| 2016/0131596 A1 | 5/2016 | Cadieux, Jr. et al. |
| 2016/0131629 A1 | 5/2016 | Cadieux, Jr. et al. |

FOREIGN PATENT DOCUMENTS

| | | |
|---|---|---|
| DE | 102011007666 A1 | 10/2012 |
| EP | 0146299 A1 | 6/1985 |
| EP | 0223446 A2 | 5/1987 |
| EP | 657028 A1 | 6/1995 |
| EP | 0897762 A2 | 2/1999 |
| EP | 2715320 A2 | 4/2014 |
| GB | 2091416 | 7/1982 |
| JP | S61290057 A | 12/1986 |
| JP | S6459095 A | 3/1989 |
| JP | H04-00473 | 1/1992 |
| JP | H0666728 A | 3/1994 |
| JP | H0666728 A | 3/1994 |
| JP | H09-309845 | 12/1997 |
| JP | 2000-273757 | 10/2000 |
| JP | 2002505426 A | 2/2002 |
| JP | 2002513155 A | 5/2002 |
| JP | 2005-037398 | 2/2005 |
| JP | 3907042 | 1/2007 |
| JP | 2009-229466 | 10/2009 |
| JP | 2014512185 A | 5/2014 |
| JP | 2014515487 A | 6/2014 |
| WO | 1991017265 A1 | 11/1991 |
| WO | 9800243 A1 | 1/1998 |
| WO | 6624104 A2 | 11/1999 |
| WO | 9957417 | 11/1999 |
| WO | 1999057417 A2 | 11/1999 |
| WO | 2001025747 A2 | 4/2001 |
| WO | 2001025748 A2 | 4/2001 |
| WO | 2001025764 A1 | 4/2001 |
| WO | 2001025766 A1 | 4/2001 |
| WO | 2001025767 A1 | 4/2001 |
| WO | 2001025820 A2 | 4/2001 |
| WO | 2002068945 A1 | 9/2002 |
| WO | 2008049515 A2 | 5/2008 |
| WO | 2010/007390 A2 | 1/2010 |
| WO | 2012030988 A1 | 3/2012 |
| WO | 2012050844 A1 | 4/2012 |
| WO | 2012162701 A4 | 5/2013 |
| WO | 2013181286 A1 | 12/2013 |
| WO | 2014168720 A1 | 10/2014 |

OTHER PUBLICATIONS

International Search Report of International Application No. PCT/US2013/043172 dated Aug. 6, 2013.
International Search Report of International Application No. PCT/US2012/039870 dated Jan. 14, 2013.
International Preliminary Report on Patentability of International Application No. PCT/US2014/026556 dated Sep. 15, 2015.
International Preliminary Report on Patentability of International Application No. PCT/US2013/043172 dated Dec. 2, 2014.
International Preliminary Report on Patentability of International Application No. PCT/US2012/039870 dated Nov. 26, 2013.
Victoria B. Rodriguez et al., Encapsulation and Stabilization of Indocyanine Green within Poly(Styrene-Alt-Maleic Anhydride) Block-Poly(Styrene) Micelles for Near-Infrared Imaging, Journal of Biomedical Optics; Jan. 30, 2008, vol. 13 No. 1, pp. 14025-1-140025-10; XP002664215.
International Search Report & Written Opinion issued in International Patent Application No. PCT/US2015/060179, dated Feb. 8, 2016.
Office Action for corresponding Mexican Application No. MX/a/2013/013768 dated May 23, 2018 and English translation thereof.
Decision of Rejection for Japanese Application No. 2017-073848 dated Sep. 3, 2018.
Office Action dated Feb. 15, 2018 in Japanese Patent Application No. 2017-073848.
Office Action dated Mar. 29, 2016 in Japanese Patent Application No. 2014-512185.
Office Action dated Dec. 2, 2016 in Japanese Patent Application No. 2014-512185.
Notice of Allowance dated Aug. 29, 2018 in Japanese Patent Application No. 2014-512185.
Notice of Allowance dated May 16, 2018 in Canadian Patent Application No. 2,837,315.
Office Action for corresponding U.S. Appl. No. 14/883,200 dated Oct. 16, 2018.
Office Action for corresponding U.S. Appl. No. 14/938,561 dated Dec. 7, 2018.

OIL DETECTION PROCESS AND APPARATUS

RELATED APPLICATION

This patent application is a Divisional of U.S. Ser. No. 15/653,377, filed Jul. 18, 2017, This patent application is a Continuation of U.S. Ser. No. 14/994,972 filed on Jan. 13, 2016, now U.S. Pat. No. 9,733,197, which is a Divisional of U.S. Ser. No. 13/482,771, filed on May 29, 2012, now U.S. Pat. No. 9,244,017, which is a continuation-in-part of U.S. Ser. No. 13/338,971, filed on Dec. 28, 2011, now U.S. Pat. No. 9,080,987, and claims priority to U.S. Provisional Application Ser. No. 61/490,403, filed on May 26, 2011, the contents of each are hereby incorporated by reference in their entirety.

FIELD

Disclosed herein is an on-line inspection process and apparatus for detection of oil and/or grease (lubricant) contamination on tobacco, tobacco products, food pharmaceuticals, packaging, and other consumer goods and products, and a light wavelength converting material for taggant applications and quantitative diagnostics.

ENVIRONMENT

In the processing and packaging of consumer products and products designed to provide tobacco enjoyment, oils, greases and lubricants may inadvertently come into contact with the product being produced.

In the case of products designed to provide tobacco enjoyment, tobacco leaf is processed prior to the time that it is provided as final product. For example, leaf may be contacted by machinery during harvesting, curing and transport to a stemmery. When leaf is provided in strip form at a stemmery, and cut or otherwise shredded to the desired size, it is possible for oils, greases and lubricants to inadvertently come into contact with the tobacco. Likewise, lubricants used in operating the various machines used in the processing of the tobacco can come inadvertently into contact with that tobacco. The sources of lubricant contamination can vary, such as when a particular piece of machinery or component of that piece of machinery fails to operate in an optimum fashion.

Lubricants may inadvertently come into contact with tobacco due to leakage of lubricants through gaskets or seals, from sliding mechanisms, from drum systems, from gear boxes, from pumps, from sealed rolling bearing units, from chains and belts, and the like. Lubricants are used in conditioning cylinders, threshers, separators, redryers, receivers, feeders, conveyors, cutters, blenders, tobacco presses and other such pieces of equipment that are commonly used in tobacco stemmeries, and in tobacco primary processing operations.

Lubricants of similar compositions are used throughout the various stages of tobacco treatment and cigarette manufacture. Heretofore, it has been difficult for the cigarette manufacturer to detect the presence of oil in its tobacco and/or its cigarettes and to locate the source of a particular lubricant once it has been detected.

It would be advantageous if the inspection of tobacco and tobacco products for the presence of a lubricant or the like could be conducted on-line, that is, in real time during the production process, with the capability to identify the source, once it has been detected.

SUMMARY

In one aspect, disclosed is a process for detecting oil or lubricant contamination in a manufactured product, the process comprising adding a fluorescent taggant to oils or lubricants contained in processing machinery for said product; conveying said product past an infrared detection apparatus; irradiating said product with infrared radiation from said detection apparatus as it passes the detection apparatus; and detecting infrared radiation emitted from said irradiated product.

In another aspect, disclosed is a process for detecting oil or lubricant contamination in a tobacco product, the process comprising adding a fluorescent taggant to oils or lubricants contained in tobacco processing machinery; conveying tobacco product past an infrared detection apparatus; irradiating said tobacco product with infrared radiation of a first wavelength from said detection apparatus as it passes the detection apparatus; and detecting infrared radiation emitted from said irradiated tobacco product.

In yet another aspect, disclosed is a system for localization of oil contamination, comprising a tipping machine for tobacco rods having an infrared detection apparatus comprising a high intensity infrared light source directed at tobacco rods and a high speed NIR spectrometer sensor tuned to detect an of a second wavelength emitted signal from an Indocyanine Green (ICG) complex disposed in said oil.

In a further aspect, disclosed is a process for detecting lubricant contamination in a product produced by a manufacturing operation and/or processing operation. The process includes adding a first taggant to a lubricant of a first machine of the operation, adding a second taggant to a lubricant of a second machine of the operation, and irradiating the product and detecting radiation emitted from the product responsive thereto, the detecting step including distinguishing the first taggant from the second taggant so as to discern the source of lubricant contamination.

The irradiated product absorbs the original radiation and re-emits radiation of a different wavelength than the original radiation, which then may be detected as disclosed herein.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Figure 1:
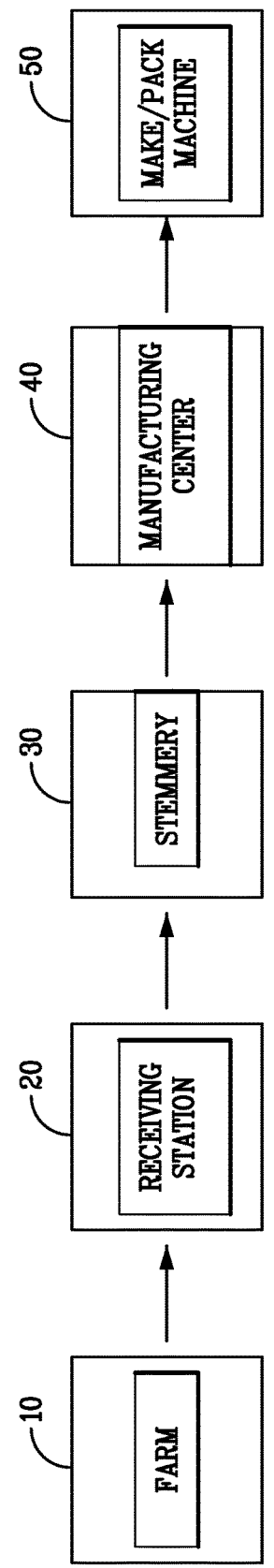
FIG. 1 is a block diagram showing the various stages in the process of cigarette manufacturing.

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-8, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Disclosed herein are new oil soluble, light wavelength-converting, preferably upconverting, compositions for taggant applications and quantitative diagnostics in connection with lubricants, such as by way of non-limiting example, the detection of errant lubricants on product that comes into contact with lubricated machinery. Other taggant applications are contemplated, including, but not limited to, anti-counterfeiting, brand protection, or verification that a machine contains a correct lubricant, and other possible applications. A detection system enables the development of near real time, low cost, compact, portable and highly sensitive detection, monitoring and diagnostics of modifications to manufacturing process systems in real world environments. It is the unique process (e.g. the conversion of visible light to infrared light, infrared to visible light and the up-conversion of infrared to higher energy infrared) that enables high sensitivity detection against almost any sample or environmental background.

Using the system, theoretical particle detection ($10^{-23}$ mol) of molecules added to analytic mixtures can be achieved through the use of on-line verification methods and even handheld detection applications. Detection sensitivity of $10^{-20}$ mol is possible in a variety of detection schemes, and even direct visual detection of $10^{-14}$ mol sensitivity has been demonstrated using a hand held 3.0 to 9.0 volt laser diode system against backgrounds of various colors and compositions. The narrow emission bandwidths and small particle size of these materials enable the simultaneous detection of multiple analytes (i.e. multiplexed assays).

In one form, the detection system disclose herein can be used in many processes and for consumer products which are susceptible to lubricant contamination during the manufacturing process, such as for example in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, frozen foods and other comestibles, and the like. Further applications could include clothing, furniture, lumber or any other manufactured or packaged product wherein an absence of oil is desired.

According to the present invention, a detectable taggant compound is added to the various lubricants used in manufacturing and processing machinery, and advantageously taggant compounds having different characteristics are added into the lubricants at different processing locations, such that detection of one or more of these taggant compounds can enable rapid identification of the location of the source of lubricant contamination in the manufactured product.

Advantageously, the taggant compound is one which is detectable by fluorescence when it is exposed to particular wavelengths of light. In particular, a suitable taggant is one which absorbs energy at one wavelength and fluoresces/emits at a different wavelength. Such materials are well-known in the art as Stokes-shifting materials, and have recently found increasing use in inks for security marking of documents, such as banknotes and the like, to render such documents less susceptible to counterfeiting or copying. However, some conventional Stokes-shifting and anti-Stokes conversion materials are composed of inorganic compounds, such as doped rare earth metal particles, such as those described in U.S. Published Patent Application No. 2010/0219377, which are insoluble in lubricants. It would be advantageous if taggant compounds could be formulated to be soluble or dispersible in oils or lubricants.

In one form, the taggant may be an organic compound comprised of purified crystals from naturally occurring chlorophyll. Suitable naturally-occurring chlorophyll crystals include Chlorophyll A (CAS number 1406-65-1) and Chlorophyll B (CAS number 519-62-0). These taggants are known as being down-converting or fluorescent, and are sensitive to a particular narrow wavelength of IR light (680 nanometers). The taggant emits back this particular of light at a different wavelength (715 nanometers). A similar compound may be a benze-indolium perchlorate or a benze-indolium tosolyate. Such materials absorb around 670 nanometers and emit at a wavelength of 713 nanometers. Another material with down-conversion properties is Indocyanine Green (ICG). The chemical structure for Chlorophyll A is provided below.

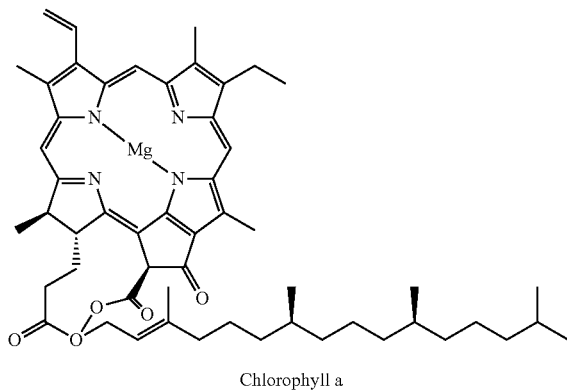

Chlorophyll a

Since this compound is an organic chemical, it is readily dissolved in oils and lubricants.

In another form, an oil-soluble fluorescent material has been developed based on Indocyanine Green (ICG), the chemical structure of which is provided below.

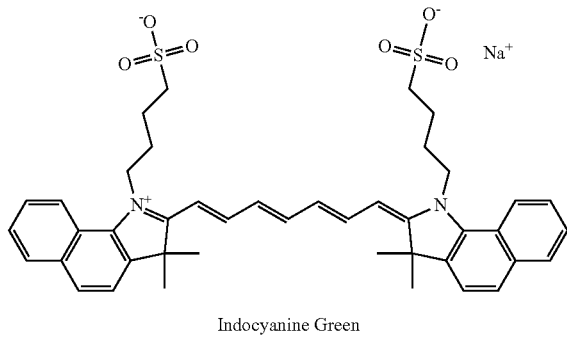

Indocyanine Green

ICG is sodium 4-[2-[(1E,3E,5E,7Z)-7-[1,1-dimethyl-3-(4-sulfonatobutyl)-benzo[e]indol-2-ylidene]hepta-1,3,5-trienyl]-1,1-dimethyl-benzo[e]indol-3-ium-3-yl]butane-1-sulfonate, an infrared fluorescing compound currently used in the medical industry for imaging cells and blood flows in the human body, which in its conventional form is water-soluble.

The newly developed taggant is an ICG-complex available from Persis Science LLC, Andreas Pa. The chemical structure for a tetrabutylammonium chloride complexation of ICG is provided below and analytical structural information is provided in FIG. 8.

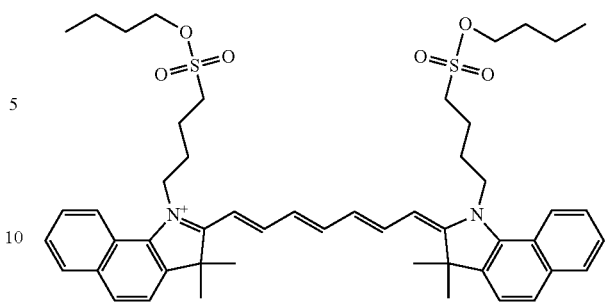

Figure 4:
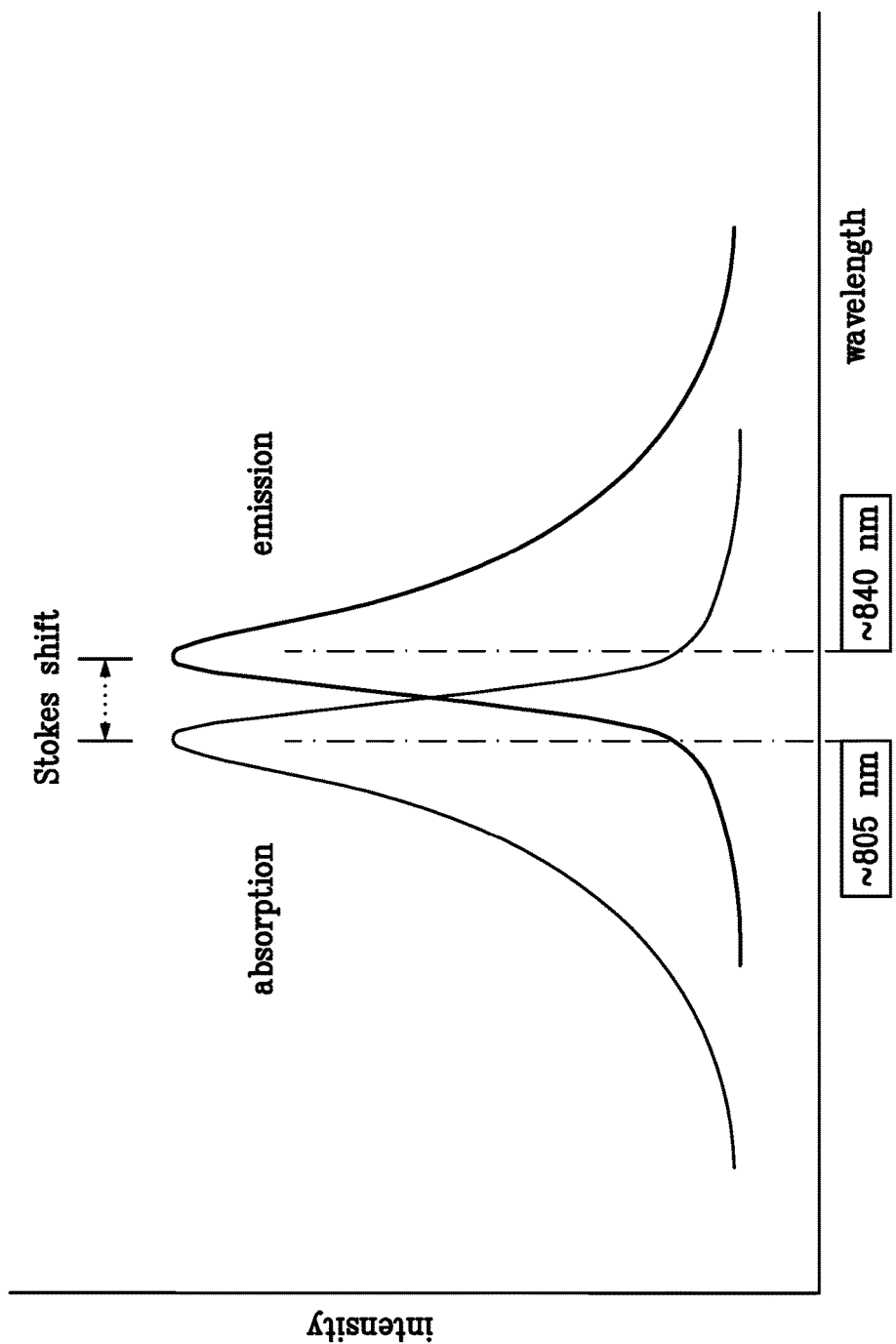
FIG. 4 is a representation of the infrared absorption and emission peaks of the Indocyanine Green (ICG) complex taggant, illustrating the Stokes-shift.

The new ICG-complex is sensitive to a particular narrow absorption band of IR light between about 760 to about 810 nanometers (FIG. 6), and emits light at a different band between about 810 to about 840 nanometers (FIG. 7), with discrete absorbance peaks at about 785 nanometers (FIG. 7) and 805 nanometers (FIG. 4), and a discrete emission peak at about 840 nanometers (FIG. 4).

The ICG complex can be added to oils or lubricants in the amounts of approximately 1 ppb to 5%, preferably a range of 1 ppm to 2000 ppm, based on the weight of the lubricant.

Figure 2:
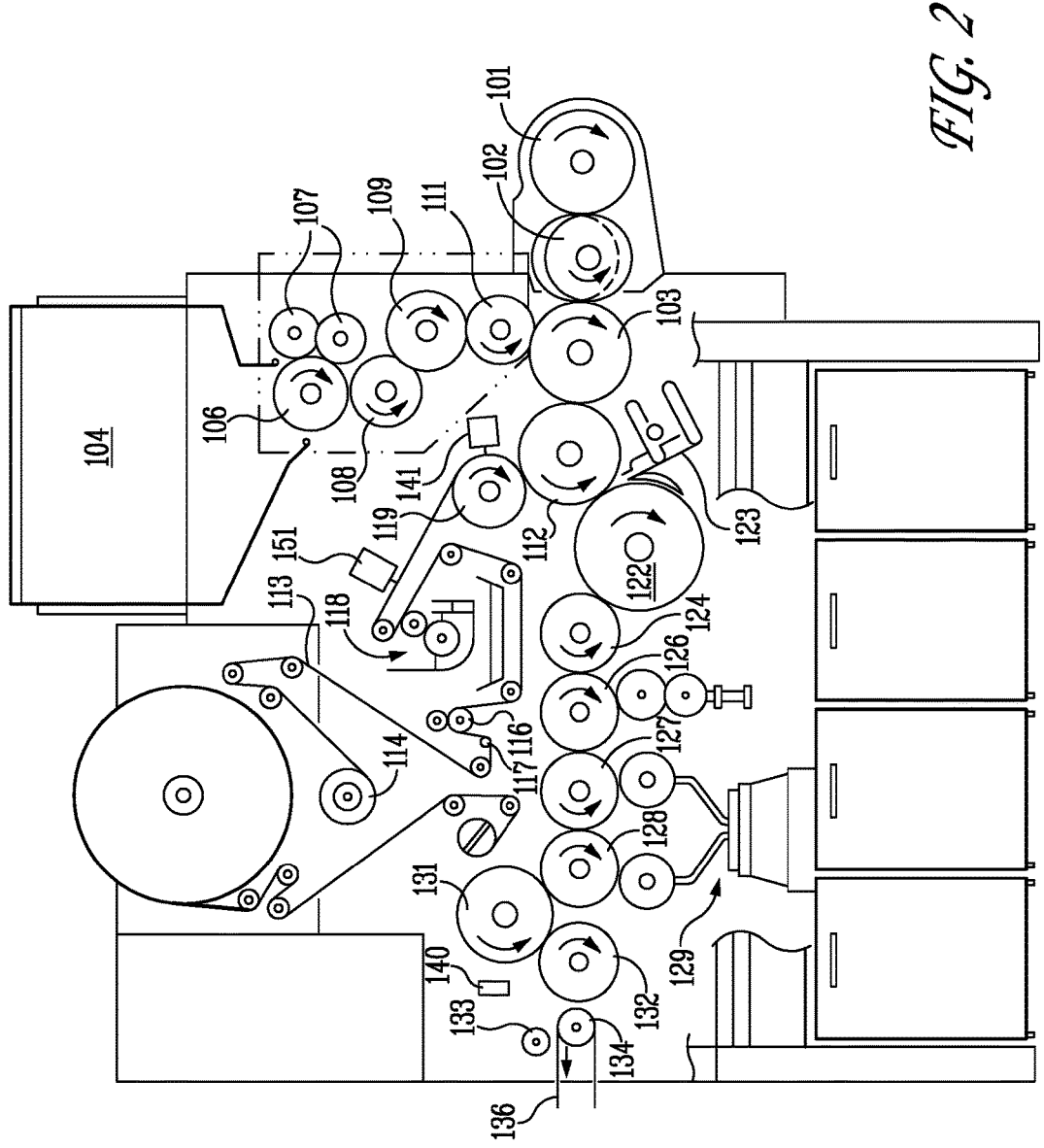
FIG. 2 is a diagrammatic front elevational view of a filter tipping machine which includes the detection apparatus of the present invention.

Additionally, the nature of the ICG complexing agent can be modified to impart one or more secondary NIR emission wavelengths adjacent to the major emission peak at 840 nanometers. By utilizing such variations in the complexing agent, and adding differently complexed ICG compounds in lubricants at differing locations in the overall process, a single detector can be located at the end of the process, and when contamination is detected, the contaminated product can be removed from the process and further analyzed for the secondary NIR emission peaks, to determine the location of the source of contamination. FIG. 2 is an illustration of the absorption and emission peaks of a modified ICG-complex, showing a secondary emission peak of a longer wavelength on the shoulder of the primary emission peak.

In one form, the detection system of the present invention can be used in many processes and for consumer products which are susceptible to lubricant contamination during the manufacturing process, such as for example in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, cosmetics, foods and other consumer goods, and the like. Further applications could include clothing, furniture, finished wood or lumber or any other manufactured or packaged product wherein an absence of oil spotting is desired.

In one form, the detection system utilizes near-infrared (NIR) emission, wherein a high intensity IR light source is directed at tobacco products and emitted IR light from the taggant is gathered and analyzed using a high speed NIR spectrometer sensor tuned to detect the emission signal from the particular taggant added to the oil. Adequate measures are made to prevent the detector from being able to see the excitation wavelength. This is done through the use of proper filters placed over the detectors. The light from the laser is pulsed at a frequency of about 800 Hz and the detector is inversely pulsed to detect the taggant. NIR light can penetrate into various materials, such as tobacco rods, to a depth of several millimeters, even enabling subsurface inspection of finished cigarettes. The high speed NIR sensor can detect tagged oils/lubricants at speeds of over about 2,000 feet per minute or 4,000 feet per minute or more. In the production of cigarettes, the high speed NIR sensor can detect tagged oils/lubricants of finished cigarettes at a rate of 15,000 per minute (about 4,920 feet per minute), or even at a rate of 20,000 per minute (about 6,560 feet per minute).

The high-speed detector comprises an IR laser diode that is used to excite the taggant at its "absorption" frequency and a sensor that is tuned to receive light at the taggant's "emission" frequency. If the sensor detects the presence of the taggant, it can change the state of its output contacts. These output contacts can be used to stop the manufacturing equipment and set an alarm and/or to reject the oil contaminated product.

The taggant can be added to process machinery lubricants at concentrations between about 10 ppm and 100 ppm, typically at a concentration of about 50 ppm, based on the weight of the oil/lubricant. At these taggant concentration levels the detection system can detect as little as 10 microliters of oil, or even as little as 1 microliter of tagged oil.

However, in order to provide for easier treatment of oils or lubricants already in place within various machines, it can be more convenient to formulate a master batch of the taggant in any particular oil, wherein the taggant is mixed at higher concentrations in the base oil/lubricant, such as from about 0.1 to about 5 wt % taggant, or even from about 0.2 to about 2 wt % taggant, in a balance of the base oil/lubricant. A portion of such tagged master batch is then easily transported and added to oils/lubricants which are already in place in the machines to be treated, for example by adding a small amount of the tagged master batch to the oil sump of the machine.

When the taggant is not an oil-soluble taggant, such as when it is an inorganic particle, an optional surfactant or dispersant additive can be added in an amount effective to facilitate dispersion of the taggant particles in the base oil. Such surfactants/dispersants are well-known in the art and their identities need not be repeated herein.

The NIR emission detectors can be placed virtually anywhere along the process, such that a signal received by a detector at a known location will indicate oil contamination in the processed material almost immediately, readily indicating the location of the source of contamination directly upstream of the detector.

In an alternative form, the nature of the ICG complexing agent can be modified to impart one or more secondary NIR emission wavelengths adjacent to the major wavelength peak at 840 nanometers. By utilizing such variations in the complexing agent, and adding differently complexed ICG compounds in lubricants at differing locations in the overall process, a single detector can be located at the end of the process, and when contamination is detected, the contaminated product can be removed from the process and further analyzed for the secondary NIR emission peaks, to determine the location of the source of contamination.

Referring now to FIG. 1, a block diagram showing the various stages in the process of cigarette manufacturing is presented. As shown. Tobacco is first harvested at farm 10, which, in the case of tobacco for use in cigarette manufacturing or the production of moist smokeless tobacco (MST), will be harvested at least in part by machinery. Tobacco in the form of leaf is baled and received at a receiving station 20 from farm 10. Again, the opportunity exists for the tobacco bale to come into inadvertent contact with lubricated machinery at receiving station 20. The baled tobacco may be transferred to a stemmery 30 wherein large stems are removed by machines to produce destemmed tobacco. The destemmed tobacco is packed into bales which are then stored for a suitable time period of up to several years.

Destemmed tobacco is then transferred to manufacturing center 40, wherein various types of tobacco strip may be machine blended according to a predetermined recipe. The blended tobacco may be treated by adding various flavorants to provide a cased tobacco, which is then cut to provide tobacco "cut filler." Various other types of tobacco can be added to the cut filler including puffed tobacco, reconstituted tobacco, tobacco reclaimed from rejected cigarettes, and the like, to provide a final product blend. The blend may be then fed to make/pack machine 50, which includes a continuous cigarette rod making apparatus. The continuous rod is then cut, optionally tipped, and packed, typically through the use of high-speed machinery.

As may be appreciated from the above description, in tobacco processing, tobacco comes into contact with machinery at many different points in the overall process, such as machinery used during the growing and harvesting operations on the farm, handling equipment at the receiving station or auction house, machinery in the stemmery, on conveyors, conditioners, cutters and silos in the primary manufacturing centers, and ultimately on makers, tippers and packers in the make/pack manufacturing centers. By utilizing a different taggant in the lubricants of the machinery at each of these locations, the discrete source and/or location of contamination can be readily determined by inspection/detection of the finished product.

In FIG. 2, a typical filter tipping machine 100 for tobacco rods is shown, which comprises a frame supporting a rotary drum-shaped conveyor 101 having axially parallel peripheral flutes each of which contains a single plain cigarette C of unit length. The cigarettes C in the neighboring flutes of the conveyor 101 are staggered with reference to each other as seen in the axial direction of the conveyor 101, so that they form two rows each adjacent a different axial end of the conveyor 101. Successive plain cigarettes C of one row are transferred into successive flutes of one of two rotary drum-shaped aligning conveyors 102, and the cigarettes C of the other row are transferred into successive flutes of the other aligning conveyor 102. The conveyors 102 advance the respective plain cigarettes C at different speeds and/or through different distances to align each cigarette C of one row with a cigarette C of the other row not later than at the transfer station at which successive axially aligned pairs of plain cigarettes C (with a clearance between their neighboring (inner) ends) are admitted into successive axially parallel peripheral flutes of a rotary drum-shaped assembly conveyor 103.

A magazine or hopper 104 at the top of the frame of the filter tipping machine contains a supply of filter rod sections of six times unit length. The outlet of the magazine 104 admits discrete filter rod sections of six times unit length into successive axially parallel peripheral flutes of a rotary drum-shaped severing conveyor 106. The latter cooperates with two axially and circumferentially staggered rotary circular knives 107 which subdivide each oncoming filter rod section of six times unit length into groups of three coaxial filter rod sections of double unit length each.

Successive groups are delivered into the flutes of a composite rotary drum-shaped staggering conveyor 108 which moves at least two filter rod sections of each group relative to each other and relative to the third filter rod section in a circumferential direction and transfers successive filter rod sections of double unit length into successive flutes of a rotary drum-shaped shuffling conveyor 109. The latter cooperates with suitable cams or the like (not shown) to form a single row of aligned filter rod sections which are advanced sideways into successive flutes of a rotary drum-shaped combined accelerating and inserting conveyor 111. The conveyor 111 inserts discrete filter rod sections of double unit length into the aforementioned clearances between successive pairs of plain cigarettes in the oncoming flutes of the assembly conveyor 103 so that each such flute of the conveyor 103 which has advanced beyond the transfer station between the conveyors 103 and 111 contains a group of three coaxial rod-shaped articles including two axially spaced-apart tobacco rods of unit length and a filter rod section of double unit length between them. Successive groups are caused to advance between two cams or the like (not shown) which cause the tobacco rods to move axially toward each other so that their inner ends abut the respective ends of the filter rod section between them. The thus condensed or shortened groups are transferred into successive flutes of a rotary drum-shaped transfer conveyor 112.

The frame of the filter tipping machine further supports an expiring reel 114 for a supply of an elongated web or strip 113 which is convoluted onto the core of the reel 114. The web 113 is advanced lengthwise by rollers 116 which cause it to advance over the pronounced edge of a conventional curling tool 117, and a rotary drum-shaped suction conveyor 119 thereupon causes the web 113 to advance into and beyond a paster 118 serving to coat one side of the web with a film of a suitable adhesive. The adhesive-coated leader of the web 113 is severed at requisite intervals at the periphery of the suction conveyor 119 to yield a succession of adhesive coated discrete portions or uniting bands which are attached to successive groups of rod-shaped articles in the flutes of the transfer conveyor 112. Each uniting band extends along and slightly beyond both axial ends of the respective filter rod section of double unit length.

Successive groups of rod-shaped articles (each such group carries a uniting band) are transferred onto a drum-shaped rolling or wrapping conveyor 122 which cooperates with a normally stationary rolling member 123 to convolute the uniting bands around the respective filter rod sections and around the adjacent inner ends of the respective pairs of plain cigarettes C of unit length. The thus obtained filter cigarettes C of double unit length are delivered into the flutes of a rotary drum-shaped adhesive drying or setting conveyor 124 which, in turn, delivers successive filter cigarettes C of double unit length into the peripheral flutes of a rotary drum-shaped subdividing conveyor 126 cooperating with a circular knife to sever each filter cigarette C of double unit length midway across the tubular wrapper (converted or rolled uniting band) so that a conveyor 127 of a turn-around device 129 receives pairs of coaxial filter cigarettes C of unit length. The device 129 inverts one filter cigarette C of each pair end-for-end so that the single-length filter mouthpieces of all filter cigarettes C face in the same direction not later than on a further conveyor 128 of the turn-round device 129 and the inverted and non-inverted filter cigarettes C form a single row of parallel cigarettes C which are caused to move sideways.

The conveyor 128 delivers successive filter cigarettes C of the single row into successive flutes of at least one inspection drum 131 which is followed by a combined testing and reject drum 132. As may be appreciated, the present invention contemplates the case in which each flute of an inspection drum of a tipping machine receives two cigarettes. Any reference herein to a flute of an inspection drum receiving a single cigarette is meant to cover such a case as well. The inspection drum 131 can advance successive filter cigarettes C of unit length past one or more NIR testing devices 140 each which irradiates cigarettes C with IR radiation having a wavelength of about 805 nm, and detects reflected IR radiation at wavelengths at or about 840 nm (in the case where the taggant is an ICG complex). As is conventional, inspection drum 131 may also be employed to detect loose ends, air leaks around filter tips, etc. The reject drum 132 receives a signal from and cooperates with control device 140 to eject those filter cigarettes C which are detected to contain one or more of the taggants according to the present invention. A take-off conveyor (e.g., an endless belt or chain conveyor having an endless flexible element 136 trained over several pulleys, sheaves or sprocket wheels 134 of which only one is actually shown in FIG. 2) cooperates with a decelerating device 133 and serves to advance satisfactory filter cigarettes C of unit length to a next processing station, e.g., into a reservoir or into a packing machine or to another destination.

Figure 3:
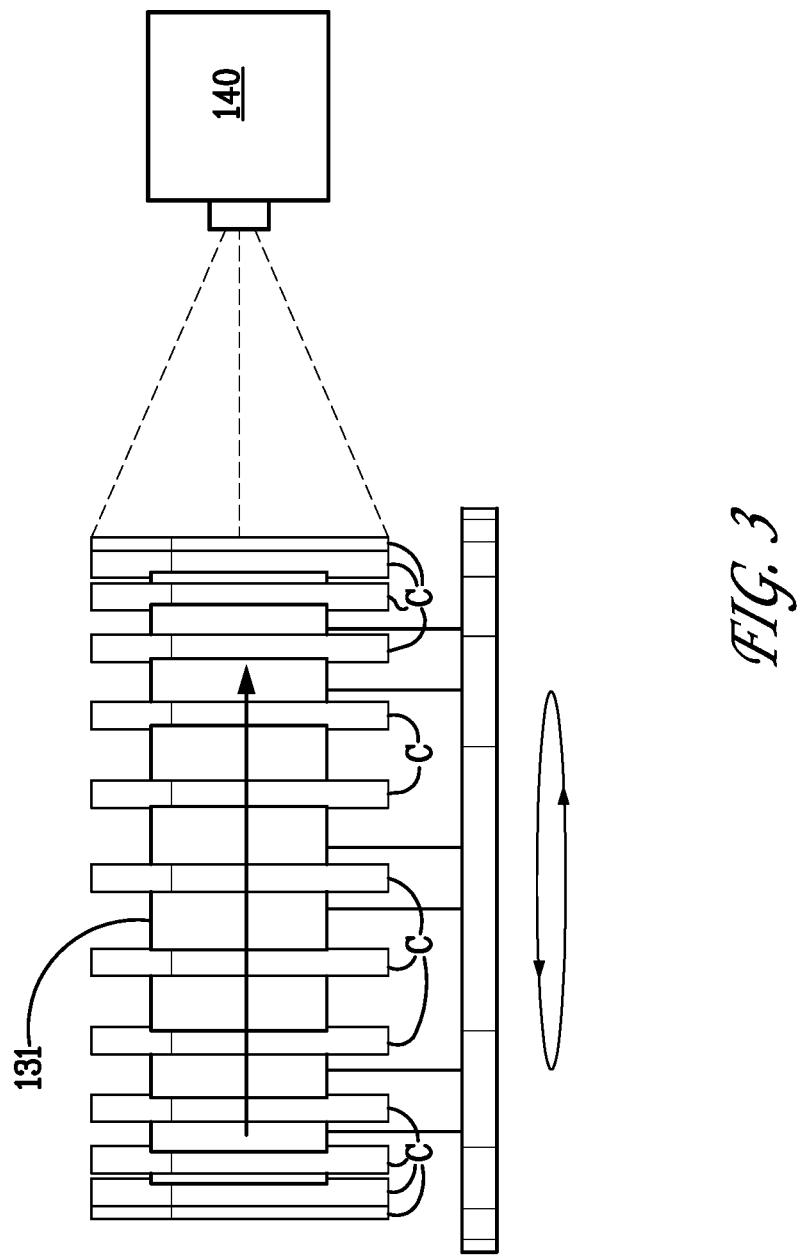
FIG. 3 is a detailed diagrammatic view of the detection apparatus of the present invention.

FIG. 3 is a detailed illustration of inspection drum 131 which holds a series of tipped cigarettes C on a fluted wheel via vacuum. Each cigarette C is irradiated with IR radiation at a wavelength of about 805 nm along the entire length of the cigarette C as it passes IR detection device 140, and instantaneously emits IR radiation at wavelengths at or about 840 nm from any tagged oil which might be contained in the cigarette C. The emitted IR radiation is in turn detected by IR detection device 140, which sends a signal to reject drum 132 to reject the identified cigarette C.

Figure 5:
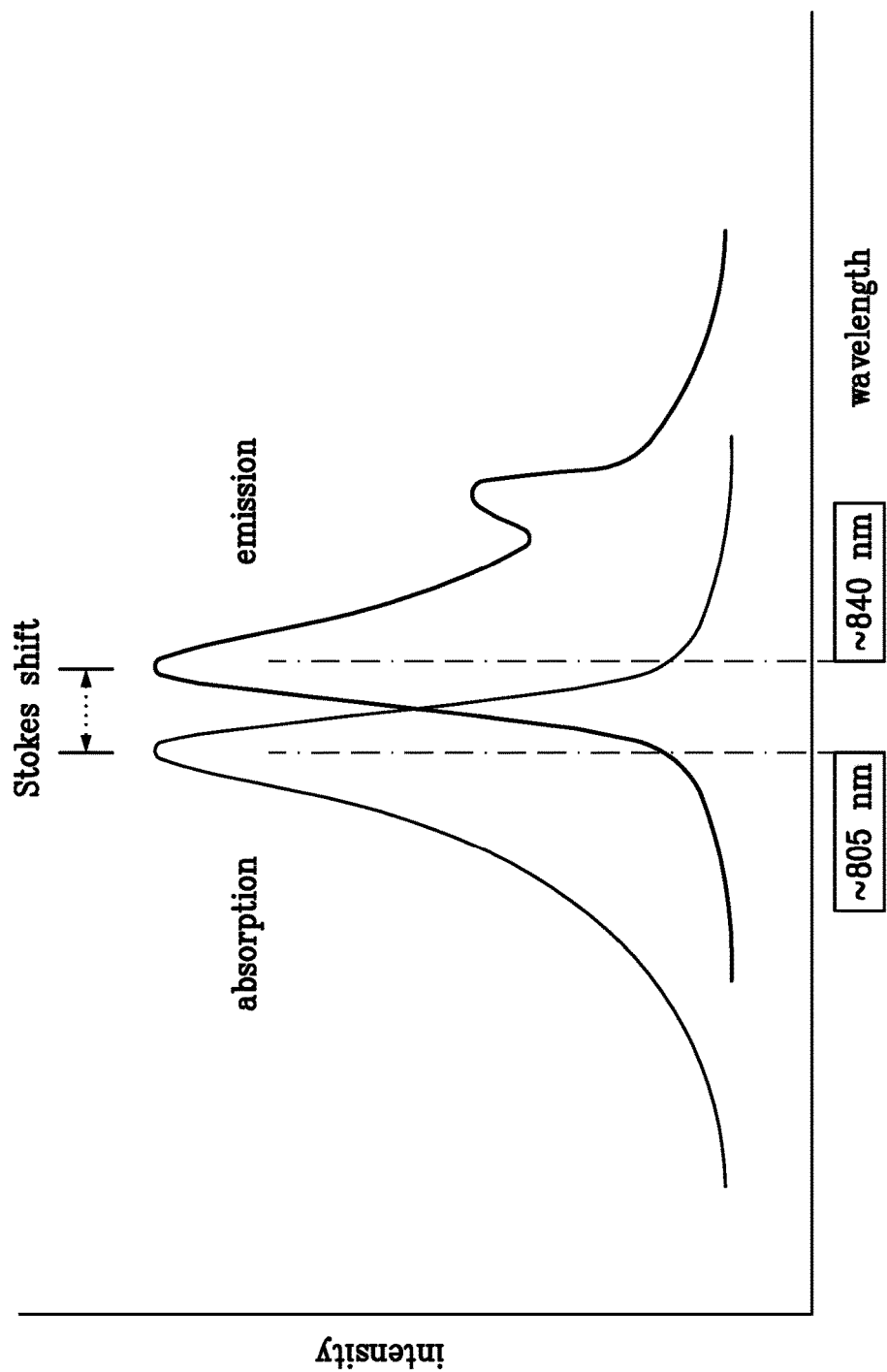
FIG. 5 is a representation of the infrared absorption and emission peaks of a modified ICG-complex, illustrating a secondary emission peak.
Figure 6:
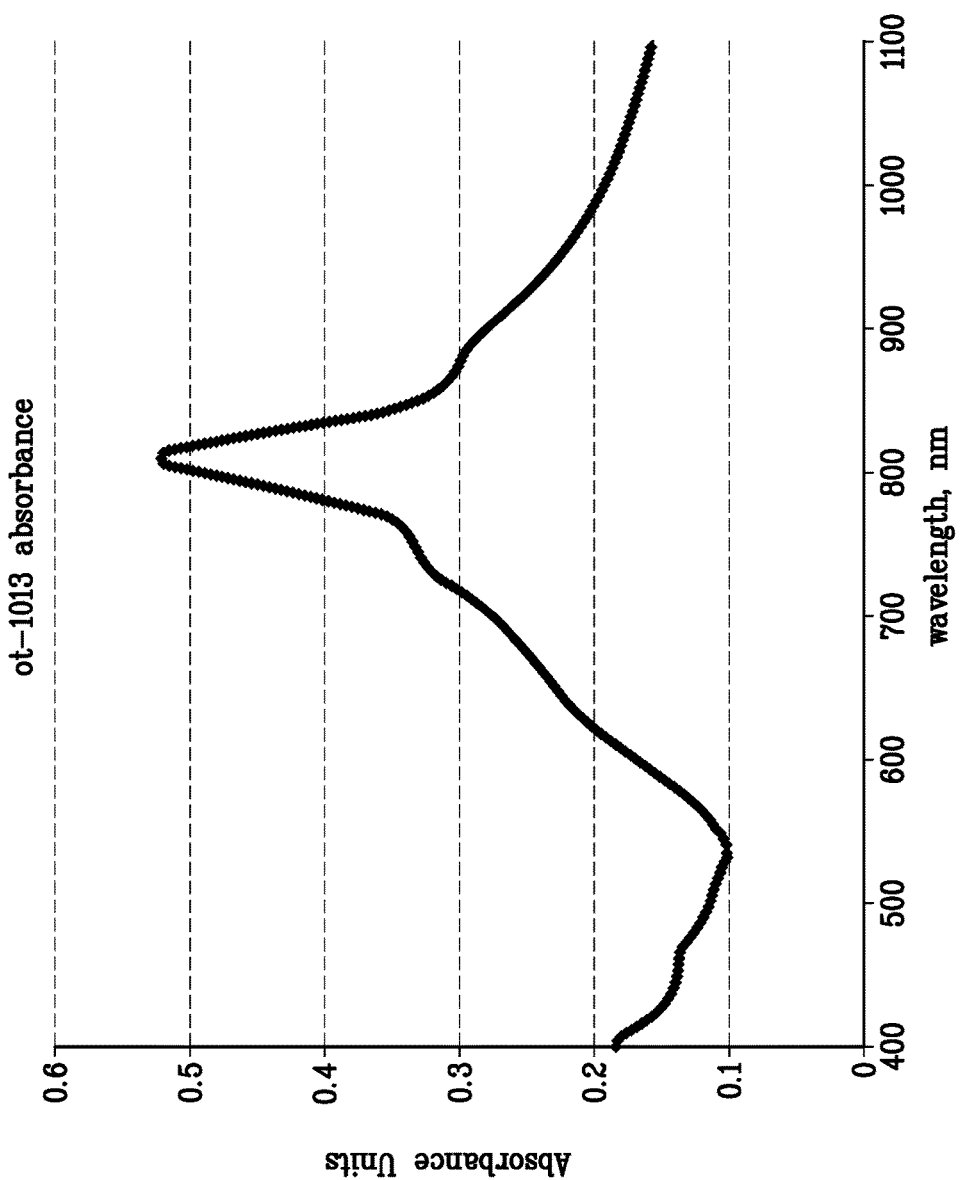
FIG. 6 is a representation of the infrared absorption peak for the modified ICG-complex of Example 1.
Figure 7:
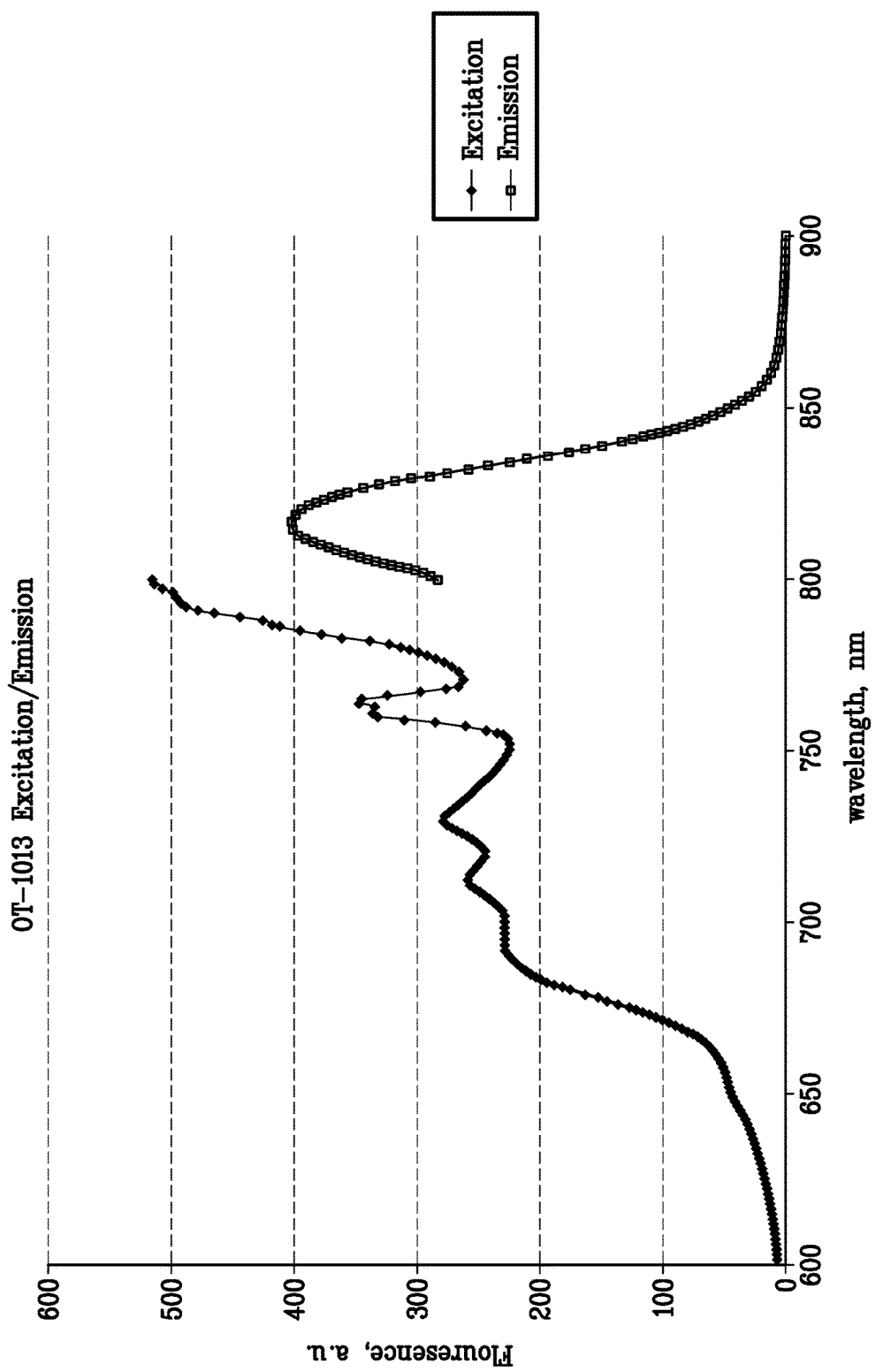
FIG. 7 is a representation of the infrared excitation and emission peaks for the modified ICG-complex of Example 1.
Figure 8:
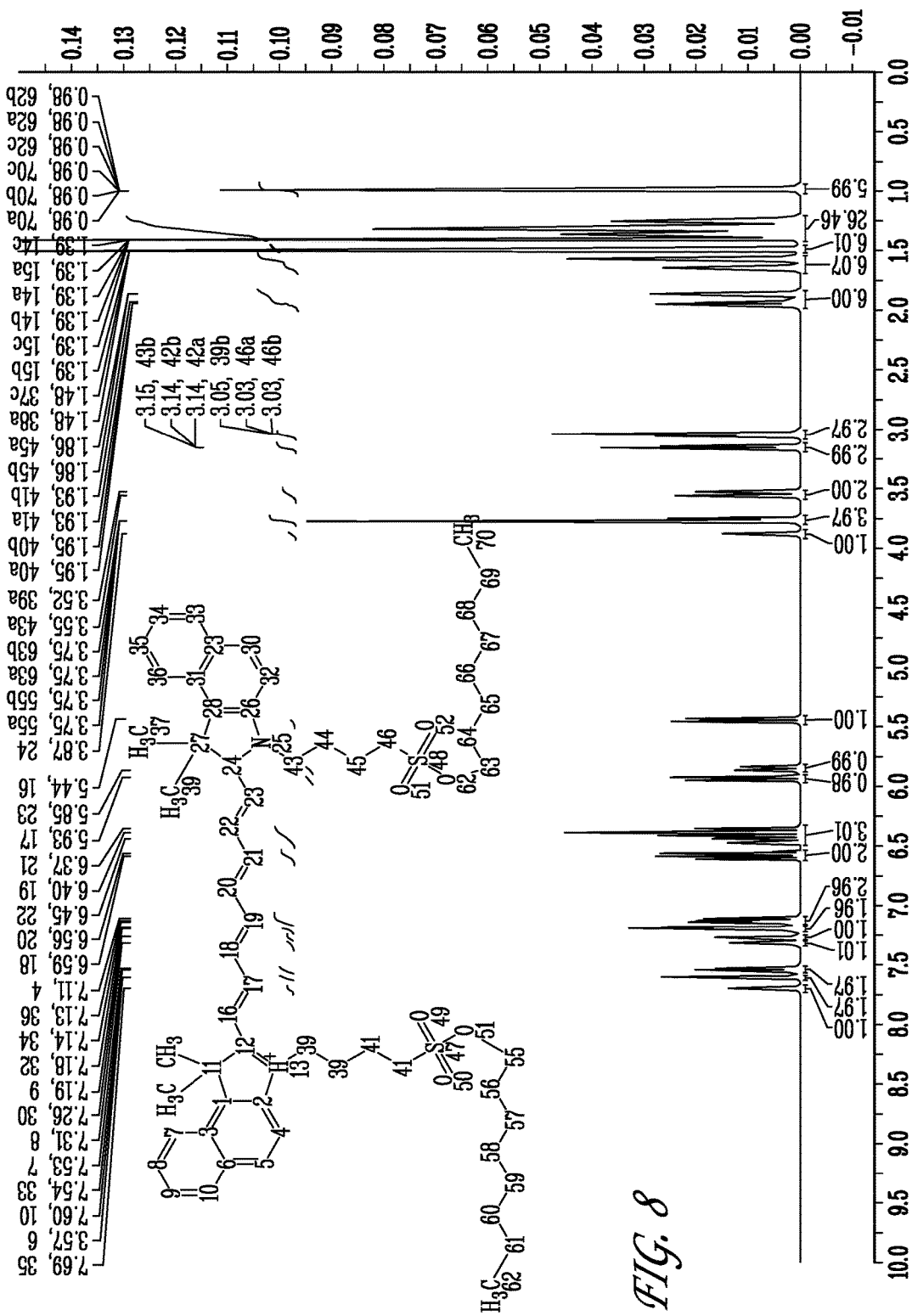
FIG. 8 is an H-nuclear magnetic resonance scan of the ICG-complex according to this invention.

FIG. 4 is an illustration of the absorption and emission peaks of the presently disclosed ICG-complex taggant, and FIG. 5 an illustration of the absorption and emission peaks of a modified ICG-complex, showing a secondary emission peak of a longer wavelength on the shoulder of the primary emission peak.

In one form, when the NIR detection device detects the presence of the taggant primary emission peak, the identified cigarette is rejected and ejected from the system. Subsequent to ejection, the cigarette can be re-analyzed with another NIR detection device which can identify the secondary wavelength peaks from any of the variety of differently-complexed ICG taggants, so as to determine the source of lubricant contamination throughout the system.

In another form, a process for detecting oil or lubricant contamination in a manufactured product produced from raw materials is provided. The process includes the steps of adding a first taggant to an oil or lubricant of a machine for preparing raw materials for a manufacturing operation, adding a second taggant to an oil or lubricant of a machine used in a manufacturing operation for manufacturing the product, conveying the product past a detection apparatus adapted to distinguish the first taggant from the second taggant so as to discern the source of oil or lubricant contamination (i.e., whether the source of oil is from production of a raw (or direct) material or from the production of the final product of which the raw material is a part). In one form, for example and not by way of limitation, the first taggant is added to the oil or lubricant of a machine for preparing raw materials for shipping. Further, for example and not by way of limitation, the second taggant may be added to the oil or lubricant of a packaging machine. The product may be irradiated with infrared radiation from the detection apparatus as it passes the detection apparatus and infrared radiation emitted detected from the irradiated product. It is envisioned that if a plurality of machines are involved to produce a raw material, then a plurality of taggants would be utilized individually as to each of them. Likewise, if a plurality of machines is involved to produce the final product, then a plurality of taggants would also be utilized individually as to each of them.

Specific forms will now be described further by way of example. While the following examples demonstrate certain forms of the subject matter disclosed herein, they are not to be interpreted as limiting the scope thereof, but rather as contributing to a complete description.

EXAMPLES

Example 1

500 mg of complexed ICG (Product No. OT-1013, available from Persis Science LLC of Andreas Pa.) is dispersed into 1.0 kg of Klüberoil 68 using a speedmixer. Klüberoil 68 is available from Klüber Lubrication North America L.P., Londonderry, N.H. The material is mixed for 10.0 minutes at a speed of 2100 RPM. The resulting concentrate is slowly added to an additional 100.0 kg of Kluberoil 68 while stirring under high speed dispersion. A sample of the material is placed into a Shimadzu 5301 Fluorometer and the excitation and emission spectrographs are recorded. When excited at a wavelength of 785, a strong infrared emission is noted from 810 nanometers to 960 nanometers. See FIG. 6 for a representation of the infrared absorption peak for the modified ICG-complex of Example 1 and FIG. 7 for a representation of the infrared excitation and emission peaks for the modified ICG-complex of Example 1.

Example 2

The above example is modified slightly using a tetrabutylammonium bromide complexation of an Infrared dye available, IR830 available from Sigma-Aldrich of St. Louis, Mo. After mixing, it is noted that the material will produce fluorescence around 833 nanometers when excited with approximately 0.5 mW of 785 light.

Example 3

Upconverting nanoparticles, MED C-19 ($Yb_2O_3:Er^{3+}$), were obtained from Persis Science, LLC in a slurry format in DMSO. The DMSO was dialyzed from the aqueous phase leaving the particles in aqueous phase. The particles were dried and dispersed into Kluberoil 68 using a Speedmixer. The dispersion was measured optically using a Spex Fluorolog-3. The oil suspension was excited at 970 nm and the detection occurred in the visible from 400 to 700 nm to determine the presence of the tagged oil.

Example 4

0.5 wt % of a europium chelate, available from Honeywell Corporation under the trade name of CD-335, was incorporated into 99.5 wt % of Lubriplate 220 oil using a horizontal media mill. Adequate detection was achieved using UV LED's at a wavelength of 363 nm and an APD detector with a 600 nm-700 nm notch filter.

Example 5

1.0 wt % of an infrared absorbing dithiolene dye commercially available from Epolin, Inc—358 Adams St. Newark N.J. 07105, was dissolved via mixing with 99 parts of Kluber Oil 220 under nitrogen with a stir bar for 5 hours. The resulting mixture was analyzed for infrared absorption. The absorption occurred from 800 nm to 1200 nm with a peak at around 1060 nm. The detection was achieved by contrast imaging with a Cognex In-Sight vision system and using a Monster LED light system with a wavelength of 850 nm. A Midwest optical filter 850 bandpass was used to isolate the absorption.

As may be appreciated, other tobacco- and non-tobacco-related consumer product applications can benefit from the invention disclosed herein. Contemplated tobacco-related applications include cigars, cigarillos, MST, pouched tobacco products. dry snuff, chewing tobacco and snus. The taggants disclosed herein may be applied in accordance with these teachings to various machines and machine modules that execute various manufacturing operations at points along the manufacturing process of interest. The systems and methods disclosed herein can be modified for compatibility with such applications.

While the present invention has been described and illustrated by reference to particular forms, those of ordinary skill in the art will appreciate that the invention lends itself to variations not necessarily illustrated herein. For this reason, then, reference should be made solely to the appended claims for purposes of determining the true scope of the present invention.

We claim:

1. An inspection station for detecting oil or lubricant contamination in a manufactured product, comprising:
   (a) a conveyor for advancing manufactured product; and
   (b) an infrared detection apparatus, said infrared detection apparatus including:
      (i) a high intensity infrared light source for directing at the manufactured product, and
      (ii) a high speed NIR spectrometer sensor tuned to detect an emitted signal from a taggant disposed in the oil or lubricant,
   wherein said infrared detection apparatus is positioned proximate said conveyor for advancing manufactured product at a distance effective to enable detection of emitted IR radiation as each advancing successive manufactured product is irradiated.

2. The inspection station of claim 1, wherein the taggant is an Indocyanine Green complex.

3. The inspection station of claim 1, wherein the taggant disposed in the oil or lubricant is a Stokes-shifting taggant, which absorbs infrared radiation at a first wavelength and fluoresces at a second wavelength, different from said first wavelength.

4. The inspection station of claim 3, wherein said first wavelength is about 805 nanometers and said second wavelength is about 840 nanometers.

5. The inspection station of claim 1, wherein the taggant is oil or lubricant soluble.

6. The inspection station of claim 5, wherein the taggant is added to the oil or lubricant at a concentration of between about 10 ppm and 100 ppm.

7. The inspection station of claim 6, wherein the taggant is added to the oil at a concentration of about 50 ppm.

8. The inspection station of claim 1, wherein a detection level of the tagged oil or lubricant is less than about 10 microliters.

9. The inspection station of claim 8, wherein a detection level of the tagged oil or lubricant is less than about 1 microliter.

10. The inspection station of claim 1, wherein the infrared detection apparatus detects a primary emission peak of the taggant.

11. The inspection station of claim 10, wherein at least a portion of the manufactured product displaying the primary emission peak of the taggant are segregated for offline detection of a secondary peak associated with a source of oil or lubricant contamination.

12. The inspection station of claim 1, wherein the infrared detection apparatus is effective to detect subsurface oil or lubricant contamination.

13. The inspection station of claim 1, wherein the infrared detection apparatus is effective to detect oil or lubricant contamination at manufacturing speeds of 2,000 feet per minute or more.

14. The inspection station of claim 13, wherein the infrared detection apparatus is effective to detect oil or lubricant contamination at manufacturing speeds of about 4,000 feet per minute or more.

15. The inspection station of claim 14, wherein the infrared detection apparatus is effective to detect oil or lubricant contamination at manufacturing speeds of about 4,920 feet per minute.

16. The inspection station of claim 14, wherein the infrared detection apparatus is effective to detect oil or lubricant contamination at manufacturing speeds of about 6,560 feet per minute.

17. The inspection station of claim 1, wherein said inspection station includes an inspection drum of a cigarette tipping machine, said inspection drum having a plurality of flutes and said manufactured product is a tobacco rod.

18. The inspection station of claim 17, wherein each flute receives one or two tobacco rods for inspection.

19. The inspection station of claim 17, wherein said inspection drum advances successive tobacco rods past said high speed NIR spectrometer.

20. The inspection station of claim 17, wherein said tipping machine further comprises a reject drum, said reject drum configured to receive a signal from a control device to eject tobacco rods detected to contain one or more of the taggants.

21. The inspection station of claim 1, which is effective to correlate the emitted IR radiation with a machine leaking said oil or lubricant upstream of said inspection station.

* * * * *